United States Patent [19]

Krause et al.

[11] Patent Number: 5,717,128
[45] Date of Patent: Feb. 10, 1998

[54] PREPARATION OF ALKYLESTERS OF O,O-DIALKYL-4-PHOSPHONO-2-METHYL-2-BUTENOIC ACID AND ALKYL ESTERS OF 4-HALO-2-METHYL-2-BUTENOIC ACID CONTAINING A HIGH PERCENTAGE OF E ISOMERS

[75] Inventors: Wolfgang Krause, Brühl; Hansgeorg Ernst, Speyer; Joachim Paust, Neuhofen; Udo Rheude, Otterstadt; Walter Dobler, Heidelberg, all of Germany

[73] Assignee: BASF Aktiengesellschaft, Ludwigshafen, Germany

[21] Appl. No.: 535,637

[22] Filed: Sep. 28, 1995

[30] Foreign Application Priority Data

Oct. 4, 1994 [DE] Germany ............ 44 35 421.5

[51] Int. Cl.⁶ .................. C07F 9/40; C07C 69/65
[52] U.S. Cl. ........................... 558/125; 560/219
[58] Field of Search ................... 558/125; 560/219

[56] References Cited

U.S. PATENT DOCUMENTS

| | | | |
|---|---|---|---|
| 3,163,669 | 12/1964 | Stilz et al. | 558/125 X |
| 3,806,540 | 4/1974 | Martel et al. | 260/486 |
| 4,543,417 | 9/1985 | Schmeider et al. | |

FOREIGN PATENT DOCUMENTS

| | | |
|---|---|---|
| 32 44 272 | 5/1984 | European Pat. Off. . |
| 110 329 | 6/1984 | European Pat. Off. . |
| 294 774 | 12/1988 | European Pat. Off. . |
| 21 21 361 | 11/1971 | Germany . |

OTHER PUBLICATIONS

Helv. Chim. Acta 1970, pp. 383 and 394, vol. 53.
Tetrahedron 44 (1988), pp. 4713–4720.
Liebigs Ann. Chem. 1977, pp. 1146–1159.
Houben–Weyl, Methoden der Organischen Chemie, vol. 5/4, pp. 361, 367 f and 387f and 898–9 (1952).
Houben–Weyl, vol. 5/3, p. 898 ff (1952).
Helv. Chim. Acta 1966, pp. 369–390.

*Primary Examiner*—Michael G. Ambrose
*Attorney, Agent, or Firm*—Keil & Weinkauf

[57] ABSTRACT

A process for the preparation of alkyl esters of O,O-dialkyl-4-phosphono-2-methyl-2-butenoic acid containing a high percentage of E isomers, wherein the corresponding alkyl esters of 2-hydroxy-2-methyl-3-butenoic acid are caused to react with PBr$_3$ or PCl$_3$ at temperatures ranging from 0° to 80° C. in the absence of pyridine and, if desired, the resulting mixture comprising predominantly alkyl esters of 4-halo-2-methyl-2-butenoic acid is caused to react with trialkyl esters of phosphorous acid at temperatures ranging from 70° to 140° C. The end products are desirable C$_5$ building blocks for polyene syntheses or preceding stages.

8 Claims, No Drawings

PREPARATION OF ALKYLESTERS OF 0,0-DIALKYL-4-PHOSPHONO-2-METHYL-2-BUTENOIC ACID AND ALKYL ESTERS OF 4-HALO-2-METHYL-2-BUTENOIC ACID CONTAINING A HIGH PERCENTAGE OF E ISOMERS

The invention relates to an advantageous process which is simple to carry out on an industrial scale for the preparation of alkyl esters of 0,0-dialkyl-4-phosphono-2-methyl-2-butenoic acid containing a high percentage of E isomers (referred to below, for the sake of simplicity as alkyl esters of 0,0-dialkyl-4-phosphonotiglic acid) as well as the advantageous preparation of alkyl esters of 4-halo-2-methyl-2-butenoic acid containing a high percentage of E isomers (hereinafter referred to as esters of 4-halotiglic acid).

The methyl and ethyl esters of 0,0-dialkyl-4-phosphonotiglic acid are desirable building blocks for Horner-Emmons reactions for the synthesis of polyenes. They are required, for example, for the preparation of the β-apo-8-carotenic acid esters or β-apo-4-carotenic acid esters (cf DE-A 3,244,272; CH-A 850,137 oder Helv. Chim. Acta 1959, pp. 864–70), which are desirable natural dyes, or for the preparation of crocetinic diesters (cf Angew. Chem. 72 (1960), pp. 911–15).

The alkyl esters of 4-halotiglic acid can be converted to the corresponding 4-triarylphosphonium derivatives as well as to the alkyl esters of 0,0-dialkyl-4-phosphonotiglic acid, which are desirable C$_5$ building blocks for Wittig reactions (cf Liebigs Ann. Chem. 1977, pp. 1146–59, particularly pp. 1150–51).

A known method of preparing 4-bromo-2-methyl-buteno comprises the reaction of esters of tiglic acid or angelica acid with N-bromosuccinimide in halogenated hydrocarbons under exposure to light (cf Beilstein, 4th Supplement Vol. 2, pp. 1555 and Helv. Chim. Acta 1970, pp. 383, and 394).

Disadvantages of this process are the moderate selectivities achieved as well as the technically very elaborate reaction conditions required.

Liebigs Ann. Chem. 1977, pp. 1146–59 discloses a process for the preparation of the ethyl ester of 4-chloro-2-methyl-2-butenoic acid by heating ethyl vinyl lactate with thionyl chloride. Disadvantages of this process are the moderate yields, the use of a large excess of the halogenating agent, as well as the liberation of large amounts of SO$_2$ gas, which constitutes a serious problem for industrial processes. Furthermore, Tetrahedron 44 (1988), pp. 4713–20 discloses a process for the preparation of the methyl ester of 0,0-diethyl-4-phosphonotiglic acid in which pyruvic acid is caused to react with vinylmagnesium bromide to produce vinyllactic acid at temperatures ranging from −10° to −5° C., this then being converted to the methyl ester with diazomethane, which methyl ester, following chromatographic purification over SiO$_2$, is caused to react with phosphorus tribromide to produce the methyl ester of 4-bromotiglic acid in the presence of pyridine in diethyl ether acting as solvent at approximately 0° C., the latter methyl ester then being converted to the methyl ester of diethyl-4-phosphonotiglic acid with the triethyl ester of phosphorous acid. Disadvantages of this process are the necessity of operating at very low temperatures, the use of large amounts of solvents as well as the co-use of toxic pyridine during the reaction with phosphorus tribromide as well as the necessity of employing SiO$_2$ chromatography for the purpose of isolating crude ester of 4-halotiglic acid. In spite of the unreasonably high degree of elaboration implemented in a process to be carried out on a large scale and the problems occurring with recycling of the additives and auxiliaries there are obtained only yields of 35% of theory, based on pyruvic acid used.

Furthermore, EP 294,774, DE-A 3,244,273 and EP-A 110,329 have disclosed processes for the preparation of the esters of 4-halo-2-methyl-2-butenoic acids of the general formula III by dehydrohalogenation of 3,4-esters of dihalobutanoic acids. A disadvantage of these processes is the use of elementary bromine or chlorine, which involves the necessity for elaborate engineering and safety measures. In addition the esters of 4-halotiglic acid are isolated as isomeric mixtures having E:Z ratios of only 1:1–3:1, whereas a virtually isomer-free E C$_5$ building block is required for the synthesis of the aforementioned β-apocarotenic acid esters, which show a 100% E configuration.

Furthermore, Houben-Weyl, Methoden der Organischen Chemie, Vol. 5/4, pp. 361 et seq particularly pp. 367 et seq, 387 et seq and Vol. 5/3, pp. 898 et seq discloses that tertiary allyl alcohols can be rearranged to form the corresponding allyl halides with phosphorus tribromide or phosphorus trichloride only with more or less complete allyl rearrangement, whilst primary allyl alcohols react directly to form the corresponding halides (cf Helv. Chim. Acta 1966, pp. 369–90).

The yields are generally moderate and in some cases reach ca 80%, especially in the case of unsaturated allyl alcohols, but are in most cases distinctly less (Houben-Weyl, Methoden der Organischen Chemie, Vol. 5/4, pp. 398–9). It is also stated to be advantageous to add tertiary amines, especially pyridine.

It was the object of the present invention to provide processes for the preparation of alkyl esters of 4-halotiglic acid and alkyl esters of 0,0-dialkyl-4-phosphonotiglic acid, which yield these products in an industrially simple manner and in as high a yield as possible and with the avoidance of the aforementioned drawbacks of the prior art, using readily available starting materials and carried out in the absence of toxic reaction auxiliaries such as pyridine.

We have now found, surprisingly, that the alkyl 2-hydroxy-2-methyl-3-butenoates readily obtainable from the plant protectant Ronilan® on a large scale as intermediates (cf EP-A 11,855) can be caused to react with phosphorus tribromide or phosphorus trichloride to produce alkyl esters of 4-halo-2-methyl-2-butenoic acid without the use of pyridine and advantageously also without the use of solvents, at moderate temperatures, giving very good yields and very good E:Z selectivities, which products can in turn be converted to the alkyl 0,0-dialkyl-4-phosphono-2-methyl-2-butenoates in an industrially simple manner in very good yields and very good E:Z selectivities.

Thus the invention relates to a process for the preparation of alkyl esters of 0,0-dialkyl-4-phosphono-2-methyl-2-butenoic acids of the general formula I

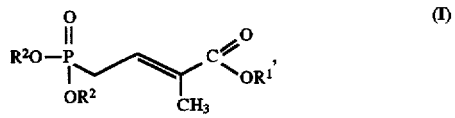

in which R$^1$ and R$^2$ stand for methyl or ethyl, containing a high percentage of E isomers, wherein A. the corresponding alkyl 2-hydroxy-2-methyl-3-butenoate of the general formula II

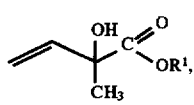

is caused to react at temperatures ranging from 0° to 80° C. and preferably from 20° to 70° C., in the absence of pyridine and preferably in the absence of appreciable amounts of solvents, with phosphorus tribromide or phosphorus trichloride to form a mixture of an ester of 4-halo-2-methyl-2-butenoic acid of the general formula III and an alkyl 2-halo-2-methyl-3-butenoate of the general formula IV

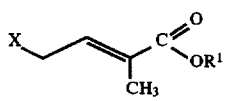

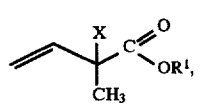

in which $R^1$ has the aforementioned meaning and x stands for chlorine or bromine, and B. the resulting mixture is caused to react at temperatures ranging from 70° to 140° C. with a trialkyl ester of phosphorous acid of the general formula V

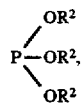

in which $R^2$ has the above meanings.

The invention further relates to a process for the preparation of alkyl esters of 4-halo-2-methyl-2-butenoic acid of the general formula III

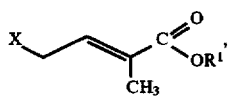

in which $R^1$ stands for methyl or ethyl and X denotes chlorine or bromine, containing a high percentage of E isomers, wherein the corresponding alkyl 2-hydroxy-2-methyl-3-butenoate of the general formula II

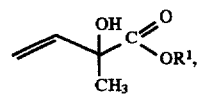

is caused to react with phosphorus tribromide or phosphorus trichloride at temperatures ranging from 20° to 80° C. and preferably from 60° to 80° C., in the absence of pyridine and preferably in the absence of appreciable amounts of a solvent.

When carrying out this process on an industrial scale a great advantage is gained when the reaction proceeds throughout at moderate temperatures and in the absence of solvents or additives, such as the toxic pyridine, since in this way the waste balance can be distinctly improved. The only marked by-product which is formed is the harmless phosphorous acid. Particularly surprising is the very large amount of E isomer of the formula III in the allyl rearrangement which is an advantage for subsequent processing to form apocarotenic acid esters. Another surprising feature is the fact that the isomeric alkyl 2-halo-2-methyl-3-butenoates of the formula IV formed as by-products are also converted, in the subsequent reaction with a trialkyl ester of phosphorous acid (Arbusov reaction), to 0,0-dialkyl-4-phosphono-2-methyl-2-butenoic acid esters containing a high percentage of E isomers desirable for Horner-Emmons reactions.

To carry out the process stage A. it is general to proceed by metering phosphorus tribromide or phosphorus trichloride to the alkyl 2-hydroxy-2-methyl-3-butenoates of the general formula II in the absence of solvents and other auxiliaries in such a manner that temperatures of not more than 80° C. occur in the reaction mixture. It is advantageous to operate at temperatures ranging from 20° to 70° C. and, when using phosphorus tribromide, it is particularly advantageous to operate at temperatures ranging from 20° to 40° C.

The molar ratio of alkyl 2-hydroxy-2-methyl-3-butenoates of the general formula II to phosphorus trihalide is generally from 3:1 to 2.6:1, preferably from 2.9:1 to 2.7:1. The metering times for the phosphorus trihalides are 0.5-8 h, preferably 1-4 h. The metering rate depends on the facilities for dissipation of the heat of reaction. Accordingly very short metering times are possible when use is made of optimal cooling measures.

The subsequent stirring times are generally approximately 0-2 h, preferably 0.5 to 1 h, at the above temperatures.

The reaction is carried out generally in the absence of "appreciable amounts" of solvent. By the use of the expression "appreciable amounts" of solvents we wish to avoid the danger of claims excluding the addition of small amounts of solvents having no effect on the reaction. By the expression "no appreciable amounts" we mean in this case amounts not exceeding approximately 10 wt %, and preferably amounts of not more than 4 wt %.

In the process step A. the alkyl esters of 4-halo-2-methyl-2-butenoic acid of the formula III are obtained, when using phosphorus tribromide, in yields of up to approximately 90% at an E:Z ratio of from 25:1 to 40:1 in addition to approximately 1–5% of the tertiary bromide of the formula IV. Although, when using phosphorus trichloride, the alkyl esters of 4-halo-2-methyl-2-butenoic acid of the formula III are obtained only in yields of up to approximately 75–80% at an isomer ratio of from 19:1 to 25:1, there are additionally obtained approximately 10–15% of the 2-chloro-2-methyl-3-butenoates of the formula IV. Since the latter are also converted to the 0,0-dialkyl-4-phosphono-2-methyl-2-butenoic acid esters during subsequent reaction, there are obtained in the process of the invention total yields of 0,0-dialkyl-4-phosphono-2-methyl-2-butenoic acid esters of up to approximately 90%, based off alkyl 2-hydroxy-2-methyl-3-butenoate used.

To effect purification of the reaction mixture obtained in the reaction stage A., the desired product phase and the phosphorous acid phase are separated. For complete isolation of the alkyl halobutenoates of the general formula III and the isomer IV the phosphorous acid phase is again extracted with an inert solvent, such as a hydrocarbon, preferably hexane or heptane.

For subsequent conversion to the 4-phosphonotiglic acid alkyl esters of the general formula I the combined organic phases are concentrated, preferably at temperatures ranging from 40° to 50° C. and at pressures of from 250 mbar to 100 mbar.

The crude 4-halo-2-methyl-butenoic acid esters thus obtained can be converted to alkyl 4-phosphono-2-methyl-2-butenoic acid esters without further purification.

If it is desired to use the esters of 4-halo-2-methyl-2-butenoic acids for other reactions and thus obtain high-purity esters of 4-halo-2-methyl-2-butenoic acids and only small amounts of the alkyl 2-halo-2-methyl-3-butenoates of the formula IV, it advisable to carry out the reaction of the alkyl 2-hydroxy-2-methyl-3-butenoate with phosphorus tribromide or phosphorus trichloride at temperatures ranging from 20° to 80° C. and preferably from 60° to 80° C., and particularly preferably, using phosphorus tribromide, at temperatures ranging from 70° to 80° C.

To carry out the process stage B, it is general to proceed by metering the halides obtained in reaction step A. To the trialkyl phosphites of the general formula V at temperatures between 70° and 140° C., preferably between 90° and 120° C., neither solvent nor any other reaction auxiliary being necessary. The metering time is approximately 0.5–8 h, preferably 1–4 h.

The trialkyl phosphite is generally employed in amounts of from 1 to 1.1 mol of 2-hydroxy-2-methyl-3-butenoate of the formula II per mole of 2-hydroxy-2-methyl-3-butenoate of the formula II used.

The alkyl halide formed during this reaction known as the Arbusov reaction can be isolated from the reaction mixture by distillation via a suitable column to give purities of up to 99% and can be re-used.

The crude alkyl esters of 0,0-dialkyl-4-phosphono-2-methyl-2-butenoic acid are then purified by distilling off low-boiling and moderately low-boiling components at temperatures ranging from 100° to 140° C. and pressures of 2–20 mbar, preferably 5–15 mbar.

In this industrially simple manner the alkyl esters of 0,0-dialkyl-4-phosphono-2-methyl-2-butenoic acid of the general formula I are isolated from the halogen compounds in yields of 85–95% and have a very high concentration of E isomers.

The E:Z ratios of the product are 19:1–30:1 when use is made of 4-bromo-2-methyl-2-butenoate at a purity of >95% and 10:1–25:1 when using 4-chloro-2-methyl-2-butenoate at comparable purity. Further purification by distillation is not necessary.

The E:Z equilibrium of alkyl 0,0-dialkyl-4-phosphono-2-methyl-butenoates is governed by temperature. Thus the undesirable Z content increases as the temperature rises. On heating to 140° C. the E:Z ratio is 15:1 and at 170° C. isomerization takes place to give an E:Z ratio of 7.4:1. At 230° C. the isomeric equilibrium is as low as approximately 5.4:1. In accordance with the aforementioned method of carrying out the Arbusov reactions it is clear that temperatures of 140° C. or less are conducive to achieving very high E contents.

The high E:Z ratios of the end products produced by the process of the invention demonstrate the great advantage over the processes of the prior art. In the process described in the aforementioned EP 294,774 there are obtained, in spite of special temperature control measures during the reaction with trialkyl ester of phosphorous acid (Arbusov reaction), alkyl esters of 0,0-dialkyl-4-phosphono-2-methyl-2-butenoic acid only in an E:Z ratio of 7:1 to not more than 8:1, and in the processes described in *J. Chem. Soc. C* 1966, pp. 2163 et seq and *J. Chem. Soc. C* 1968, pp. 1991 et seq the methyl 0,0-diethyl-4-phosphono-2-methyl-2-butenoates are obtained as isomeric mixtures having an E:Z ratio of only 3:2 despite comparable conditions during the Arbusov reaction.

With the aid of the process of the invention the desired alkyl esters of 4-halo-2-methyl-2-butenoic acids of the general formula III can be obtained in yields of up to 90% of theory as isomeric mixtures having an E:Z ratio of 18:1–40:1 and the alkyl esters of 0,0-dialkyl-4-phosphono-2-methyl-2-butenoic acids are surprisingly obtained in total yields of up to 91% of theory, based on the alkyl 2-hydroxy-2-methyl-3-butenoate used, in the form of isomeric mixtures having an E:Z ratio of 1–30:1.

EXAMPLE 1 a) Preparation of Ethyl 4-bromo-tiglic Acid Ester 2274 g (15.55 mol) of a 98.6% strength ethyl vinyl lactate (EVL) were used as the initial batch at 25° C. and caused to react with 1540 g (5.69 mol) of phosphorus tribromide over a period of 2 h at 25° C. Stirring was continued at 25° C. for 1 h.

To effect hydrolysis of excess phosphorus tribromide 1.25 L of water were added over a period of 30 min at 25° C. Following brief stirring the mixture was allowed to settle and the lower phase containing the desired product ethyl bromotiglic acid ester was separated. The product obtained weighed 3300 g. The upper phosphorous acid phase was extracted once at 25° C. with 500 mL of commercial heptane. Following brief stirring the phases were separated. Water residues were removed from the combined organic phases over a period of 1 h at 45° C. and pressures of 100–50 mbar and the heptane was removed by distillation.

The composition of the crude bromo-2-methyl-butenoate mixture (as determined by GC analysis) was as follows:
4% of ethyl 2-bromo-2-methyl-3-butenoate (compound of the formula IV in which X is Br and $R^1$ is ethyl), 88.8% of 4-bromo-tiglic acid ester of the formula III (X is Br, $R^1$ is ethyl), E:Z ratio 30:1; weighed product=3250 g of crude bromobutenoate; yield 14.56 mole equivalent to 93.7% (III+IV), (based on EVL).

b) Conversion of the Crude Bromo-2-methyl-butenoate Mixture to Ethyl 0,0-diethyl-4-phosphono-tiglic Acid Ester 2899 g (17.1 mol) of 98% strength triethyl phosphite were placed in the reactor and heated to 120° C. 3250 g of crude ethyl bromo-2-methyl-butenoate mixture prepared as described under 1a were added dropwise over a period of 2 h. The reaction began immediately metering commenced. Ethyl bromide (bp 38° C.) formed during the reaction was continuously distilled off through a Vigreux column.

On completion of the addition stirring was continued for 30 min at 120° C. The crude ethyl 0,0-diethyl-4-phosphono-2-methyl-2-butenoate was freed from low-boiling components at 120° C. down to a reduced pressure of 15 mbar (bp of the low-boiling fractions 50°–60° C.).

Following removal, by distillation, of the low-boiling components the pressure was decreased, at an internal temperature of 120° C., to 5 mbar and a moderately volatile fraction was distilled off at 80° C. The residues of ethyl 0,0-diethyl-4-phosphono-2-methyl-2-butenoate remaining on cooling to 25° C. (yellowish orange oil) were used in this quality as a building block for Horner-Emmons reactions for the preparation of β-apo-carotenic acid esters. Yield and purity of the ethyl 0,0-diethyl-4-phosphono-2-methyl-2-butenoate were (as determined by GC analysis) 3819 g having a purity of 96.0% at an E:Z ratio of 25:1, equivalent to a yield of 89.3% based on EVL.

EXAMPLE 2 a) Preparation of Ethyl 4-bromo-2-methyl-2-butenoate 2274 g (15.55 mol) of a 98.6%strength EVL were used as the initial batch at 25° C. and were then caused to react with 1540 g (5.69 mol) of phosphorus tribromide over a period of 1.5 h at from 25° C. to not more than 40° C. Stirring was continued at 40° C. for 0.5 h. To effect hydrolysis of the excess phosphorus tribromide 1.0 L of water was added over a period of 30 min at 25° C. Following brief stirring the mixture was allowed to settle and the lower phase containing the desired product ethyl 4-bromo-tiglic acid ester was separated. The weighed yield was 3350 g. The upper phosphorous acid phase was extracted once at 25° C. with 500 mL of commercial heptane. Following brief stirring the phases were separated.

Water residues were removed at 50° C. and 100–50 mbar from the combined organic phases and heptane was removed by distillation.

The composition of the crude bromo-2-methyl-butenoate mixture (as determined by GC analysis) was as follows: 1.9% of ethyl 2-bromo-2-methyl-3-butenoate and 89.6% of the methyl ester of 4-bromotiglic acid at an E:Z ratio of 21:1. The weighed yield was 3317 g of crude ethyl bromobutenoate equivalent to a yield of 94.3% (III+IV) based on EVL.

b) Preparation of Ethyl 0,0-diethyl-4-phosphono-2-methyl-2-butenoate 2899 g (17.1 mol) of 98% strength triethyl phosphite were placed in the reactor and heated to 90° C. Over a period of 2 h, 3317 g of crude ethyl bromobutenoate prepared as described under 2a) were added dropwise. The reaction began immediately on commencement of metering. Ethyl bromide (bp 38° C.) formed during the reaction was continuously distilled off through a Vigreux column. On completion of the addition stirring was continued for 1 h at 90° C.

The crude ethyl 0,0-diethyl-4-phosphono-tiglic acid ester was freed from low-boiling components (bp ca 55° C.) at 120° C. down to a reduced pressure of 15 mbar.

Following removal, by distillation, of the low-boiling components the temperature was raised to 140° C. and the pressure reduced to 5 mbar at and a moderately volatile fraction was removed by distillation (bp ca 75° C.). The residues of ethyl 0,0-diethyl-4-phosphono-2-methyl-2-butenoate (yellowish orange oil) remaining after cooling to 25° C. can be further processed in this quality in Horner-Emmons reactions. Yield and purity of the product (as determined by GC analysis): 3862 g having a purity of 96.0% at an E:Z ratio of 18:1, equivalent to a yield of 90.2% based on EVL.

The temperature relationship of the isomeric equilibrium of ethyl 0,0-diethyl-4-phosphono-2-methyl-2-butenoate is demonstrated in Table 1.

TABLE 1

| T [°C.] | Purity [wt %] | E:Z ratio |
|---|---|---|
| 120 | 96.0 | 20:1 |
| 140 | 96.0 | 18:1 |
| 170 | 95.9 | 7.4:1 |
| 200 | 95.7 | 6.3:1 |
| 230 | 95.5 | 5.4:1 |

EXAMPLE 3 a) Preparation of Ethyl Chloromethylbutenoates 365.6 g (2.5 mol) of a 98.6% strength EVL were used as the initial batch heated at 70° C. and this was caused to react with 125.7 g (0.915 mol) of phosphorus trichloride over a period of 4 h at 70° C. Stirring was continued for 1 h at 70° C. and the mixture was then cooled to 25° C.

To effect hydrolysis of excess phosphorus trichloride 200 mL of water were added over a period of 30 min at 25° C. Following brief stirring the mixture was allowed to settle and the lower phase containing the desired product ethyl chloromethylbutenoate was separated.

The upper phosphorous acid phase was extracted once with 80 mL of commercial heptane at 25° C. Following brief stirring the phases were separated. From the combined organic phases water residues were removed at 45° C. and 100–50 mbar and the heptane was substantially completely removed by distillation.

The composition of the crude chloromethylbutenoate mixture (as determined by GC analysis) was as follows: 12.5% of the compound of the formula IV (X is Cl, $R^1$ is ethyl), 75.7% of 4-chlorotiglic acid ester III (X Cl, $R^1$ ethyl) at an E:Z ratio of 21:1. The weighed yield was 398.3 g of crude chloromethylbutenoate (88.2% strength) equivalent to a yield of 86.4% (III+IV) based on EVL.

b) Preparation of Ethyl 0,0-diethyl-4-phosphono-2-methyl-2-butenoate 466 g (2.75 mol) of 98% strength triethyl phosphite were placed in the reactor and heated to 120° C. Over a period of 4 h, 398.3 g of crude ethyl chloromethylbutenoate mixture prepared as described under 3a were added dropwise. Ethyl chloride (bp 13° C.) formed during the reaction was continuously removed, by distillation, through a Vigreux column into a receiver cooled to –20° C.

On completion of the addition stirring was continued for 2 h at 90° C. The crude ethyl 0,0-diethyl-4-phosphono-2-methyl-2-butenoate was liberated from low-boiling components (bp ca 55° C.) at 120° C. down to a reduced pressure of 15 mbar.

Following removal, by distillation, of the low-boiling components the pressure was reduced to 5 mbar and a moderately volatile fraction (bp ca 85° C.) was removed by distillation.

The residues of ethyl 0,0-diethyl-4-phosphono-tiglic acid ester (yellowish orange oil) remaining after cooling to 25° C. can be further processed in this quality. Yield and purity of the ethyl 0,0-diethyl-4-phosphono-tiglic acid ester (as determined by GO analysis) were: 521.4 g having a purity of 95.0% at an E:Z ratio of 20:1, equivalent to a yield of 75%, based on EVL.

We claim:

1. A process for the preparation of an alkyl ester of a 0,0-dialkyl-4-phosphono-2-methyl-2-butenoic acid of the formula I

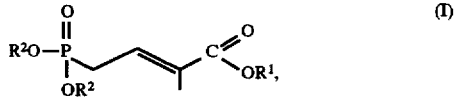

in which $R^1$ and $R^2$ stand for methyl or ethyl, containing a high percentage of E isomers, wherein A. the corresponding alkyl 2-hydroxy-2-methyl-3-butenoate of the formula II

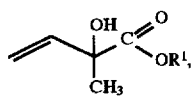

is caused to react at temperatures ranging from 0° to 80° C., in the absence of pyridine, with phosphorus tribromide or phosphorus trichloride to form a mixture of an ester of 4-halo-2-methyl-2-butenoic acid of the formula III and an alkyl 2-halo-2-methyl-3-butenoate of the formula IV

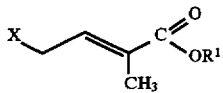

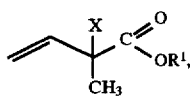

in which $R^1$ has the aforementioned meaning and x stands for chlorine or bromine, and B. the resulting mixture is caused to react at temperatures ranging from 70° to 140° C. with a trialkyl ester of phosphorous acid of the formula V

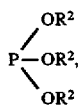

in which $R^2$ has the above meanings.

2. A process as defined in claim 1, wherein, in the process step A, the alkyl 2-hydroxy-2-methyl-3-butenoates of the formula II are caused to react with phosphorus tribromide or phosphorus trichloride in the absence of appreciable amounts of a solvent.

3. A process as defined in claim 1, wherein, in the process step A, the alkyl 2-hydroxy-2-methyl-3-butenoates of the formula II are caused to react with phosphorus tribromide or phosphorus trichloride at temperatures ranging from 20° to 70° C.

4. A process as defined in claim 1, wherein, in the process step A, the alkyl 2-hydroxy-2-methyl-3-butenoates are caused to react with phosphorus tribromide at temperatures ranging from 20° to 40° C.

5. A process for the preparation of an alkyl ester of a 4-halo-2-methyl-2-butenoic acid of the general formula III

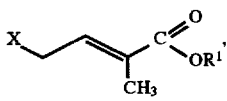

in which $R^1$ stands for methyl or ethyl and x denotes chlorine or bromine, containing a high percentage of E isomers, wherein the corresponding alkyl 2-hydroxy-2-methyl-3-butenoate of the formula II

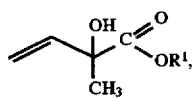

is caused to react with phosphorus tribromide or phosphorus trichloride at temperatures ranging from 20° to 80° C. in the absence of pyridine.

6. A process as defined in claim 5, wherein the alkyl 2-hydroxy-2-methyl-3-butenoate of the formula II is caused to react with phosphorus tribromide or phosphorus trichloride in the absence of appreciable amounts of a solvent.

7. A process as defined in claim 5, wherein the alkyl 2-hydroxy-2-methyl-3-butenoate of the formula II is caused to react with phosphorus tribromide or phosphorus trichloride at temperatures ranging from 60° to 80° C.

8. A process as defined in claim 5, wherein the alkyl 2-hydroxy-2-methyl-3-butenoate of the formula II is caused to react with phosphorus tribromide at temperatures ranging from 70° to 80° C.

* * * * *